US010064902B2

(12) United States Patent
Legrain-Raspaud et al.

(10) Patent No.: US 10,064,902 B2
(45) Date of Patent: Sep. 4, 2018

(54) STRAIN OF *BIFIDOBACTERIUM ANIMALIS* SSP. *ANIMALIS*

(71) Applicant: COMPAGNIE GERVAIS DANONE, Paris (FR)

(72) Inventors: Sophie Legrain-Raspaud, Le Cormier (FR); Gianfranco Grompone, Paris (FR); Sandrine Capronnier, Villemoisson sur Orge (FR); Tamara Smokvina, Orsay (FR); Marie-Christine Degivry, Le Plessis Robinson (FR); Biliana Lesic, Palaiseau (FR); Michel Neunlist, Nantes (FR)

(73) Assignee: COMPAGNIE GERVAIS DANONE, Paris (FR)

( * ) Notice: Subject to any disclaimer, the term of this patent is extended or adjusted under 35 U.S.C. 154(b) by 0 days.

(21) Appl. No.: 14/651,968

(22) PCT Filed: Dec. 10, 2013

(86) PCT No.: PCT/IB2013/060774
§ 371 (c)(1),
(2) Date: Jun. 12, 2015

(87) PCT Pub. No.: WO2014/097050
PCT Pub. Date: Jun. 26, 2014

(65) Prior Publication Data
US 2015/0320807 A1 Nov. 12, 2015

(30) Foreign Application Priority Data

Dec. 18, 2012 (WO) .............. PCT/IB2012/057431

(51) Int. Cl.
*A01N 63/00* (2006.01)
*A61K 35/745* (2015.01)
*A61K 35/747* (2015.01)
*A23C 9/123* (2006.01)
*C12R 1/01* (2006.01)
*A23L 33/135* (2016.01)
*A61K 35/00* (2006.01)

(52) U.S. Cl.
CPC .......... *A61K 35/745* (2013.01); *A23C 9/1234* (2013.01); *A23L 33/135* (2016.08); *A61K 35/747* (2013.01); *C12R 1/01* (2013.01); *A23Y 2300/21* (2013.01); *A61K 35/00* (2013.01)

(58) Field of Classification Search
None
See application file for complete search history.

(56) References Cited

U.S. PATENT DOCUMENTS

2007/0128178 A1* 6/2007 Corthesy-Theulaz ........................ A61K 35/745
424/93.45

FOREIGN PATENT DOCUMENTS

WO 2011/148220 A1 5/2010
WO 2011/148219 A1 12/2011

OTHER PUBLICATIONS

Guyonnet et al., Aliment. Pharmacol. Ther. 26: 475-486 (2007).*
Tamime, Probiotic Dairy Products, John Wiley & Sons, p. 43, 2008.*
Scardovi et al., Int. J. System. Bacteriol. 24(1): 21-28 (1974).*
Goff, The Dairy Science and Technology eBook, https://www.uoguelph.ca/foodscience/book-page/microorganisms-milk, accessed Aug. 22, 2017.*
V.S. Conlon et al., "Vasoactive intestinal peptide ameliorated intestinal barrier disruption associated with Citrobacter rodentium-induced colitis," Am. J. Physiol. Gastrointest. Liver Physiol., vol. 297, G735-G750 (2009).

* cited by examiner

*Primary Examiner* — Erin M. Bowers
(74) *Attorney, Agent, or Firm* — Arrigo, Lee, Guttman & Mouta-Bellum LLP

(57) ABSTRACT

The invention relates to a novel strain of *Bifidobacterium animals* ssp. *animalis*, which is able, inter alia, to improve the function of the enteric nervous system, and to compositions said novel strain.

11 Claims, No Drawings

STRAIN OF *BIFIDOBACTERIUM ANIMALIS* SSP. *ANIMALIS*

The invention relates to a novel strain of *Bifidobacterium animalis* ssp. *animalis*. This strain is able, inter alia, to improve the function of the enteric nervous system (ENS), in particular by increasing the vaso-active intestinal peptide (VIP) levels thereof, in order for instance to promote gut motility or barrier integrity functions. This strain can thus be used in preventing and/or reducing gastro-intestinal discomfort or gastro-intestinal disorders.

The enteric nervous system (ENS) is an integrated nervous system organized all along the gut into two major plexus with functional specific roles (Furness, *J. Auton. Nerv. Syst.*, 81(1-3):87-96, 2000). The myenteric plexus, located between the longitudinal and circular muscle, contains neurones mainly involved in the control of gastrointestinal (GI) motility. The submucosal plexus, located between the circular muscle and the mucosa, contains neurones mainly involved in the control of intestinal epithelial barrier (IEB) functions. Enteric neurons control GI functions by liberating neuromediators acting on target cells that they innervate.

With respect to the digestive system, neuromediator VIP induces smooth muscle relaxation (lower oesophageal sphincter, stomach, and gallbladder), stimulates secretion of water into pancreatic juice and bile, and causes inhibition of gastric acid secretion and absorption from the intestinal lumen. Its role in the intestine is to greatly stimulate secretion of water and electrolytes, as well as dilating intestinal smooth muscle, dilating peripheral blood vessels, stimulating pancreatic bicarbonate secretion, and inhibiting gastrin-stimulated gastric acid secretion. These effects work together to increase motility. Thus, increasing VIP beneficially improves relaxation of the muscles of the GI tract.

The intestinal epithelial barrier is constituted by a continuous monolayer of polarized specialized cells that are held together by tight junction-associated proteins such as zonula occludens-1 (ZO-1) that control barrier permeability as well as epithelial cell polarity. In vitro and in vivo studies have shown that probiotics can impact epithelial resistance and decrease permeability by modulating ZO-1 (Eun et al., APMIS, 119(1):49-56, 2011; Miyauchi et al., *J. Dairy Sci.*, 92(6):2400-8, 2009). Neuromediators synthesized by the ENS are also involved in the regulation of intestinal permeability (Hällgren et al., *Am. J. Physiol. Gastrointest. Liver Physiol.*, 275:G95-103, 1998; Hayden et al., *Am. J Physiol. Regul. Integr. Comp. Physiol.*, 278:R1589-94, 2000; Neunlist et al., *Am. J. Physiol. Gastrointest. Liver Physiol.*, 285(5):G1028-36, 2003). For instance, enhanced neuronal synthesis of acetylcholine in the colon induced by neonatal maternal separation leads to an increase of epithelial paracellular permeability in rats (Gareau et al., *Am. J. Physiol. Gastrointest. Liver Physiol.*, 293:G198-203, 2007). In contrast, vaso-active intestinal peptide (VIP) liberated by submucosal neurons increased IEB resistance by regulating the expression of tight junction protein ZO-1 in intestinal epithelial cells (Neunlist et al., *J. Intern. Med.*, 263(6):577-83, 2008). Further reinforcing the role of VIP in the regulation of barrier function is a recent study showing that VIP increased barrier resistance *Citrobacter rodentium*-induced colitis in mice (Conlin et al., *Am. J. Physiol. Gastrointest. Liver Physiol.*, 297(4):G735-50, 2009).

Several studies measured the effect of some probiotics on ENS neuromediators, including VIP. Kamm et al. (*Neurogastrointest. Motil.*, 16:53-60, 2004) disclosed effects of *Saccharomyces boulardii* on decreasing calbindin-28k (CALB) and that no effect was obtained on other neuronal markers (ChAT, VIP, SP, NF-160, etc.) of the pig jejunum. Metugriachuk et al. (*Rejuvenation Res.*, 9:342-345, 2006) disclosed that a symbiotic preparation on motility of small and large intestine in old Wistar rats significantly increased the myoelectric activity of small intestine and colon, and resulted in an increased mRNA expression of VIP but in no significant effect on VIP concentration.

It is known that bacterial strains can provide health-related benefits. Such strains are often referred to as probiotics, and are used in foods. There is a need for new strains that can be introduced in foods, with modified health-related benefits and/or with other benefits such as organoleptic properties and/or processability.

In international application WO 2011/148219, compositions including lactic acid bacteria were found to increase VIP levels in the ENS and thus improve the ENS function. These lactic acid bacteria were in particular *Lactobacillus plantarum* CNCM I-4318, *Bifidobacterium breve* CNCM I-2219, *Bifidobacterium animalis* ssp. *lactis* CNCM I-2494, and *Bifidobacterium breve* CNCM I-4321.

In this context, the inventors identified a new bacterial strain which can, inter alia, modulate the enteric nervous system especially in order to promote gut motility and barrier integrity functions, and in particular which increases the VIP level more than strains disclosed in WO 2011/148219. This strain is classified as a strain of *Bifidobacterium animalis* subspecies *animalis*, and was deposited according to the Budapest treaty with the CNCM (*Collection Nationale de Cultures de Microorganismes*) as the international depositary authority, on 6 Mar. 2012 under number I-4602.

Thus, the invention concerns strain *B. animalis* ssp. *animalis* CNCM I-4602.

The characteristics of this strain are as follows:

Colony morphology (on solid MRS+cysteine, 72 h at 37° C., anaerobic conditions): small, round and white, regular and translucent, colonies;

Microscopic morphology (on liquid MRS+cysteine, 16 h at 37° C., anaerobic conditions): thick, large, bipolar, gourds-shaped bacilli;

Fermentation of the following substrates (on an API 50 CH strip, in API MRS medium at 37° C. for 48 h): L-arabinose, D-xylose, D-galactose, D-glucose, D-maltose, D-melibiose, D-saccharose, and D-raffinose;

Biochemical identification (on an API 20 A strip, in API 20 A medium at 36° C. for 24 h): no spore, positive Gram-staining, rod-shape, acidification in presence of D-glucose, D-saccharose, D-maltose, salicin, D-xylose, L-arabinose, and D-raffinose, gelatin and esculin hydrolysis;

Detected enzymatic activities (on an API ZYM strip, at 37° C. for 4 h): esterase (C4), leucine arylamidase, cystine arylamidase, α-galactosidase, β-galactosidase, and α-glucosidase.

The present invention also encompasses the mutant strains or genetically transformed strains derived from the strain of the invention, still having activity on VIP. These mutant or genetically transformed strains can be strains wherein one or more endogenous gene(s) of the parent strain has (have) been mutated, for instance to modify some of its metabolic properties (e.g. its ability to ferment sugars, its resistance to acidity, its survival to transport in the gastro-intestinal tract, its post-acidification or its metabolite production). They can also be strains resulting from the genetic transformation of the parent strain by one or more gene(s) of interest, for instance in order to give to said strain additional physiological features, or to allow it to express proteins of therapeutic or vaccinal interest that one wishes to administer through said strains.

The strain of the invention, as well as mutants defined above, can be used as a probiotic. It can be used in preventing and/or reducing gastro-intestinal discomfort or gastro-intestinal disorders. The strain increases vaso-active intestinal peptide (VIP) levels of the enteric nervous system in a subject. It can inhibit growth of pathogens in food products and/or in a subject after administration. It can provide improved intestinal barrier properties, for example by increasing Trans Epithelial Electric Resistance (TEER) of intestinal epithelial cells. It can provide an interesting production of short chain fatty acid upon fermentation and/or upon digestion, for example an increased production or modified fatty acid composition. It can provide decreased production of gas upon fermentation and/or upon digestion. It can have an interesting resistance to gastric stress. It can provide good gastro-intestinal motility properties, for example to newborn mammals, in particular to newborn humans. It can promote maturation of the enteric nervous system and so of gut function and gastro-intestinal motility, and thus in particular decrease gastro-intestinal transit time, increase gastro-intestinal muscle contractility, improve gastro-intestinal peristalsis, prevent delayed gastric emptying, increase coordinated contractions of the gastro-intestinal system, decrease the time of meconium evacuation, decrease the time at which gastro-intestinal motility starts after birth, and allow earlier enteral feeding after birth, in newborn mammals, for example newborn humans. The strain can present good growth and/or survival in a fermented dairy product, for example in presence of vitamin K.

The invention also pertains to a composition comprising one or more other strain(s) of bacteria, probiotic or not, for instance one or more bacterial strain(s) selected from the genera *Lactobacillus, Lactococcus, Streptococcus*, and *Bifidobacteria*. In particular, this (these) other strain(s) can include one or more strain(s) of *Streptococcus thermophilus*, and/or one or more strain(s) of *Lactobacillus bulgaricus*.

This composition according to the invention can advantageously comprise at least one strain of bacteria selected from the group consisting of *Bifidobacterium breve* CNCM I-4321, *Bifidobacterium breve* CNCM I-2219, *Bifidobacterium animalis* ssp. *lactis* CNCM I-2494, *Lactobacillus plantarum* CNCM I-4318, *Bifidobacterium bifidum* CNCM I-4319, and *Lactobacillus rhamnosus* CNCM I-4316. *B. bifidum* CNCM I-4319 and *L. rhamnosus* CNCM I-4316 were disclosed in international application WO 2011/148220.

The composition of the invention can be in any form suitable for administration, in particular oral administration. This includes for instance solids, semi-solids, liquids, and powders. Liquid compositions are generally preferred for easier administration, for instance as drinks.

Examples of the composition of the invention are nutritional compositions, including food products. The composition can be for example a dairy product, preferably a fermented dairy product. Optionally, other strains of lactic acid bacteria may be present. In a preferred embodiment, strains of *Streptococcus thermophilus* and of *Lactobacillus bulgaricus* are present. The fermented product can be in the form of a liquid or in the form of a dry powder obtained by drying the fermented liquid. Preferably, the fermented product is a fresh product. A fresh product, which has not undergone severe heat treatment steps, has the advantage that bacterial strains present are in the living form. The fermented product can in particular be a dairy product, more preferably fermented milk and/or fermented whey. For instance, the nutritional composition is yoghurt, or fermented milk in set, stirred or drinkable form. The fermented product can also be a cheese, or a fermented vegetable, such as fermented soy, cereals and/or fruits in set, stirred or drinkable forms. The present nutritional composition can be a baby food, an infant milk formula or an infant follow-on formula.

The composition of the invention can also be a nutraceutical or a pharmaceutical product, a nutritional supplement or medical food.

Nutritional compositions of the invention also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

The composition according to the invention can for example comprise at least $10^5$ colony forming units (cfu), preferably at least $10^6$ cfu, per g dry weight, of the strain of the invention, *Bifidobacterium animalis* ssp. *animalis* CNCM I-4602.

In the composition of the invention, the bacterial strains, and in particular *B. animalis* ssp. *animalis* CNCM I-4602, can be used in the form of whole bacteria which may be living or not. Alternatively, they can be used in the form of a bacterial lysate or in the form of bacterial fractions. The bacterial fractions suitable for this use can be chosen, for example, by testing their properties of alleviating the effects on VIP levels of the coculture model described in the present application. Preferably, the bacterial cells are present as living, viable cells.

When the bacteria are in the form of living bacteria, the composition may typically comprise $10^5$ to $10^{13}$ cfu, preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ cfu/ml, preferably at least $10^5$ cfu/ml, more preferably at least $10^6$ cfu/ml, still more preferably at least $10^7$ cfu/ml, and most preferably at least $10^9$ cfu/ml.

The strain or the composition of the invention is especially appropriate for use in preventing and/or reducing gastro-intestinal discomfort or gastro-intestinal disorders. It can be administered to a subject suffering from intestinal discomfort or from an intestinal disorder. It is thus advantageously for use in preventing or addressing intestinal discomfort or an intestinal disorder. Such discomfort or disorders for example include gas-related discomfort or disorders, bloating, abdominal distention, abdominal pain, constipation, and in some severe aspects irritable bowel syndrome (IBS), and inflammatory bowel disease (IBD).

According to one particular aspect, the strain CNCM I-4602, or the composition according to the invention is for use for increasing vaso-active intestinal peptide (VIP) levels of the enteric nervous system in a subject. More particularly, this increase of VIP level is useful for improving gastro-intestinal motility, improving intestinal peristalsis and/or decreasing intestinal permeability, in particular in a subject having a disorder selected from the group consisting of an intestinal motility and/or permeability disorder, irritable bowel syndrome (IBS) such as IBS-C, IBS-D and IBS-PI, inflammatory bowel disease (IBD), constipation, and intestinal infections, or in a subject selected from the group consisting of elderly, infant, and obese, whose intestinal function is in general to be improved. IBS, or spastic colon, is a functional bowel disorder characterized by chronic abdominal pain, discomfort, bloating, and alteration of bowel habits in the absence of any detectable organic cause. Diarrhoea or constipation may predominate, IBS being then classified as IBS-D or IBS-C respectively, or both of them may alternate. IBS may begin after an infection, being then called IBS-PI (for post-infectious), a stressful life event, or onset of maturity without any other medical indicators.

The composition of the invention can thus be used for treating and/or preventing a disorder selected from the group consisting of an intestinal motility disorder, an intestinal permeability disorder, IBS (including IBS-D, IBS-C and IBS-PI), IBD, constipation, and intestinal infections, especially in elderly or obese people or in infants.

Details or advantages of the present invention can be found in the non limiting example below.

EXAMPLE 1: EFFECT OF LACTIC ACID BACTERIA ON NEURONAL VIP PRODUCTION IN A COCULTURE MODEL OF ENS PRIMARY CULTURES AND T84 CELLS

Differential response of primary enteric neurons on VIP production following interaction of 107 probiotic strains, including lactic acid bacteria and in particular *Bifidobacteria*, was studied.

Bacterial Strains and Growth Conditions

*Lactobacilli* were grown in Man, Rogosa and Sharpe (MRS) medium (Biokar Diagnostics, Beauvais, France), at 37° C. in aerobic conditions for 24 hours.

*Bifidobacteria* were cultured in a defined medium which consisted of a tryptone peptone (Becton Dickinson, USA) basis supplemented with glucose (Sigma, France), yeast extract (Becton Dickinson, USA), and hemin (Calbiochem, France) and grown at 37° C. in anaerobic conditions for 24 hours. *B. animalis* ssp. *lactis* strains were cultured in MRS medium (Biokar Diagnostics), supplemented with cysteine (Sigma, France), and grown at 37° C. in anaerobic conditions for 24 hours.

Obtaining a Co-Culture Model of ENS Primary Cultures and T84 Cells

A co-culture model, adapted from a model developed by Moriez et al. (*Biochem. Biophys. Res. Commun.*, 382(3): 577-82, 2009), with enteric neuron cells cultured with intestinal epithelial T84 cells was used for the screening of bacteria.

Primary cultures of rat ENS were obtained as previously described (Chevalier et al., *J. Physiol.*, 586(7):1963-75, 2008).

T84 cell line was cultured in DMEM-F12 (1:1, GIBCO) supplemented with 10% heat-inactivated FBS and 50 IU/ml penicillin and 50 µg/ml streptomycin. Cells were seeded in 12-well Transwell® filters (Corning, N.Y. USA) at a density of $2 \times 10^5$ cells/insert and cultured to obtain confluence. 24 hours before setting up the co-culture, the culture medium of T84 cells was replaced by primary ENS medium.

One day after epithelial cells arrived to confluence, Transwell® filters were transferred in the 12-well plates seeded at the bottom with enteric nervous cells. Epithelial and neuronal cells were co-cultured in the medium for epithelial cells.

Bacterial cultures were washed in PBS and re-suspended in a medium Dulbecco's Modified Eagle Medium (DMEM): Nutrient Mixture F-12 (Ham's) (1:1), containing 1% of N-2 supplement (Life Technologies, Cergy-Pontoise, France). Each strain of bacterium was tested at least in triplicate in order to perform analysis of variance. The strains were added in the filter compartment at a MOI of 40 bacteria/epithelial cell. As a control, no bacteria were added. After 8 hours of co-incubation, the filter compartment containing epithelial cells and bacteria was removed and primary ENS culture was maintained for 22 hours in the incubator (95% air, 5% $CO_2$) at 37° C. In the control wells, neuronal cells were stimulated with 40 mM KCl when VIP measurements were performed.

VIP Measurements

Then, the ENS cells were collected from the 12-well plates and used to prepare protein extracts for quantification of vaso-active intestinal peptide (VIP). For determination of intracellular VIP, the intracellular proteins were extracted using RIPA lysis buffer (Millipore, Billerica, Mass., USA) containing a protease inhibitor cocktail (Roche Diagnostics, Meylan, France). VIP was quantified using a purchased enzyme immunoassay analysis (EIA) kit (Peninsula laboratories, Bachem, SA).

Statistical Method for ENS Model

All strains VIP marker values are normalized by the negative control (T84) according to the following formula: (VIP strain strain–$VIP_{T84}$)/$VIP_{T84}$.

Strains are ranked according to their estimated normalization value coming from a mixed model with strain as fixed effect. The model gave a P-value associated to each strain estimated normalized value. If the P-value was less than 5% (<0.05), the strain effect was significant.

Results

Results are shown in Table 1 below.

TABLE 1

| Control or Bacterial species | Strain reference and/or deposit number | % VIP increase vs negative control (T84) | P value |
| --- | --- | --- | --- |
| KCl (positive control) | — | 15.7% | <0.0005 |
| Bifidobacterium animalis ssp. animalis | CNCM I-4602 | 62.5% | <0.0005 |
| Lactobacillus plantarum | CNCM I-4318 | 59.8% | <0.0005 |
| Bifidobacterium breve | CNCM I-2219 | 27.2% | 0.018 |
| Bifidobacterium animalis ssp. lactis | CNCM I-2494 | 23.5% | 0.006 |
| Bifidobacterium longum | — | 22.8% | 0.033 |
| Bifidobacterium breve | CNCM I-4321 | 22.5% | 0.008 |
| Bifidobacterium bifidum | — | 0.18% | 0.038 |
| Lactobacillus casei | — | −17.4% | 0.049 |
| Lactobacillus johnsonii | — | −19.4% | 0.03 |
| Bifidobacterium breve | — | −20.0% | 0.02 |
| Bifidobacterium breve | — | −21.6% | 0.014 |
| Bifidobacterium longum | — | −23.4% | 0.009 |
| Bifidobacterium longum | — | −24.1% | 0.008 |
| Bifidobacterium longum | — | −25.7% | 0.004 |
| Bifidobacterium longum | — | −33.1% | 0.0003 |
| Bifidobacterium longum | W11 (LMG P-21586) | −25.7% | 0.004 |
| Bifidobacterium longum | — | −35.0% | 0.0007 |

KCl, used as positive control, increased the level of VIP in average by 15.7%.

Nine strains were able to significantly increase VIP level, from 0.18 to 62.5%. Table 1 gives the results obtained for 7 of them. Among the 9 strains, *B. animalis* ssp. *animalis* CNCM I-4602 was shown to increase VIP at the highest level. There was a 62.5% increase versus the level in absence of any strain.

On another hand, it was observed that 15 strains significantly (P<0.05) decreased VIP level. The results for 10 of these 15 strains are indicated in Table 1.

The other strains tested had no significant (P>0.05) effect on VIP, including for instance *Bifidobacterium longum* NCC 2705 (CNCM I-2618), *Lactobacillus rhamnosus* GG (ATCC 53103), *Bifidobacterium infantis* UCC 3564, *Bifidobacterium longum* Bb536, *Bifidobacterium animalis* ssp. *lactic* Bi-07 (ATCC SD 5220), *Lactobacillus johnsonii* La1 (CNCM I-1225), *Lactobacillus plantarum* 299v (DSM 9843), and *Lactobacillus reuteri* SD 2112 (ATCC 55730).

The invention claimed is:

1. A composition comprising the *Bifidobacterium animalis* subspecies *animalis* strain deposited on 6 Mar. 2012 under number I-4602 with the CNCM (*Collection Nationale de Cultures de Microorganismes*) (strain *Bifidobacterium animalis* subspecies *animalis* CNCM I-4602), wherein the composition is a fermented dairy food product.

2. The composition according to claim 1, wherein the composition comprises at least $10^5$ cfu, per g dry weight, of the strain *Bifidobacterium animalis* ssp. *animalis* CNCM I-4602.

3. The composition according to claim 1, wherein the composition comprises at least $10^6$ cfu, per g dry weight, of the strain *Bifidobacterium animalis* ssp. *animalis* CNCM I-4602.

4. A method of preventing and/or reducing gastro-intestinal discomfort or gastro-intestinal disorders, comprising administering the strain *Bifidobacterium animalis* subspecies *animalis* CNCM I-4602 to a subject in need thereof.

5. The method of claim 4, wherein the strain is administered to a subject having a disorder selected from the group consisting of an intestinal motility disorder, an intestinal permeability disorder, irritable bowel syndrome (IBS), inflammatory bowel disease (IBD), constipation, and intestinal infections.

6. A method of preventing and/or reducing gastro-intestinal discomfort or gastro-intestinal disorders, comprising administering a composition according to claim 1 to a subject in need thereof.

7. The method of claim 6, wherein the composition is administered to a subject having a disorder selected from the group consisting of an intestinal motility disorder, an intestinal permeability disorder, irritable bowel syndrome (IBS), inflammatory bowel disease (IBD), constipation, and intestinal infections.

8. A method of increasing vaso-active intestinal peptide (VIP) levels of the enteric nervous system in a subject, comprising administering the strain *Bifidobacterium animalis* subspecies *animalis* CNCM I-4602 to a subject in need thereof.

9. A method of increasing vaso-active intestinal peptide (VIP) levels of the enteric nervous system in a subject, comprising administering a composition according to claim 1 to a subject in need thereof.

10. A method of improving gastro-intestinal motility, improving intestinal peristalsis and/or decreasing intestinal permeability, comprising administering the strain *Bifidobacterium animalis* subspecies *animalis* CNCM I-4602 to a subject in need thereof.

11. A method of improving gastro-intestinal motility, improving intestinal peristalsis and/or decreasing intestinal permeability, comprising administering a composition according to claim 1 to a subject in need thereof.

* * * * *